United States Patent [19]

Van der Werf et al.

[11] 3,973,909
[45] Aug. 10, 1976

[54] METHOD FOR TESTING ANTIFREEZE
[75] Inventors: Loren John Van der Werf; Myron Colman Rapkin, both of Elkhart, Ind.
[73] Assignee: Miles Laboratories, Inc., Elkhart, Ind.
[22] Filed: Apr. 20, 1972
[21] Appl. No.: 245,877

[52] U.S. Cl. ........................ 23/230 R; 23/253 TP; 252/408
[51] Int. Cl.² .................. G01N 21/08; G01N 25/06
[58] Field of Search .................. 23/230 R, 253 TP; 252/75, 74, 408; 324/30 R

[56] References Cited
UNITED STATES PATENTS

| | | | |
|---|---|---|---|
| 3,006,735 | 10/1961 | Jordan | 23/253 TP |
| 3,063,812 | 11/1962 | Collins | 23/253 TP |
| 3,616,696 | 11/1971 | Ludlow et al. | 23/253 TP |

OTHER PUBLICATIONS
"The Physical Properties and Behavior of Ethylene and Propylene Glycol and Their Water Mixtures," L. D. Polderman, Presented in Ashrae, Jan. 26–29, 1959.
*British Standard* 3150: (1959) p. 15.
Ballinger et al., J. Am. Chem. Soc. 82,; 795–798. (1960).
Getman et al., "Outline of Physical Chemistry," New York: John Wiley and Sons Inc. 450–451, (1943).

*Primary Examiner*—R.E. Serwin

[57] ABSTRACT

A method for determining the freeze point of an antifreeze-containing solution which includes simply dipping into the solution to be tested a bibulous material incorporated with a pH indicator and a buffer for maintaining the pH of the absorbed solution near or within the color change range of the indicator and comparing any apparent color change developed thereon to a color chart correlated to indicate various colors corresponding to various freeze points of antifreeze-containing solutions.

5 Claims, No Drawings

METHOD FOR TESTING ANTIFREEZE

BACKGROUND OF THE DISCLOSURE

The need for determining the freeze point of antifreeze-containing solutions is well established. Perhaps this type of determination is most commonly employed in checking the freeze resistance of automobile engine cooling systems. While this type of determination is relatively common in colder climates, the advent of high compression engines and automobile air conditioners has resulted in the addition of antifreeze to automobile cooling systems in all climates. This is now a standard procedure because antifreeze not only lowers the freezing point of the cooling system solution, it also raises the boiling point of the solution.

The commonly employed method of determining freeze points of antifreeze-containing solutions is to remove a sample of the solution and determine the specific gravity thereof by use of a hydrometer, a floating ball device or the like. In most instances, the readings of the hydrometer are correlated to freeze points because the concentration of the solution, measured by specific gravity, is usually directly proportional to the freeze point thereof. In the case of the floating ball device a number of balls are employed, each ball having a different density. The balls that sink in the solution, due to the weight of the balls and the concentration of the antifreeze in the solution, are determinative of the specific gravity of the solution. Due to the relatively large amount of sample necessary to conduct these tests, the sample is usually replaced in the container, i.e. the radiator from which the test solution was obtained, at the end of each test.

Common to each of the hereinbefore described commonly used methods is a mechanical instrument adapted to detect a property of the antifreeze-containing solution; namely the change in the specific gravity of the solution upon a variation of the concentration of antifreeze in the solution.

The mechanical instrument used with the previously described methods inherently provides the following disadvantages: it is subject to breakage and is relatively expensive, the floats thereof can become dirty and difficult to read, and a relatively large amount of sample solution is required to lift the float.

SUMMARY OF THE INVENTION

This invention relates to an improved method for determining the freeze point of an antifreeze-containing solution, the method including the steps of immersing momentarily into the solution to be tested a carrier incorporated with a pH indicator and a buffering agent, removing the carrier from the solution and comparing any color change visible in or on the carrier to a color chart standardized to provide various shades of color corresponding to various freezing points of antifreeze-containing solutions.

DESCRIPTION OF THE PREFERRED EMBODIMENT

The device involved in the method includes a bibulous carrier member having incorporated therewith a pH indicator and a buffering agent capable of stabilizing the pH of the test solution absorbed into said carrier near or within the color change range of the indicator.

The carrier member may be any suitable absorbent or bibulous material, such as filter paper, wood, fibrous synthetic material and the like. The indicator and buffering agent can be impregnated into or coated on the carrier member. The impregnated or coated carrier member can be utilized by itself or with an additional backing. It has been found that a convenient handle portion for the device can be easily prepared by forming the carrier member into strips measuring from about 4 to about 12 inches in length. A rigid or semi-rigid support or backing member may be used, in which case the carrier member may be attached to the backing member, and the latter may be elongated to form a handle portion for the test device.

The indicator may be any pH indicator responsive within the pH range of 2.0 to 6.0, and preferably within the range 3.0 to 5.0. Exemplary of indicators found suitable for the purpose of this test device are tetrabromphenol blue, tetrabromophenolphthalein ethyl ester, congo red and bromphenol blue. Tetrabromphenol blue is preferred as an indicator because of its sensitivity in ethylene glycol solution, ethylene glycol being the main constituent in most permanent type commercial antifreezes.

In determining the buffering agent of the present invention, the choice of the indicator is determinative of the choice of the buffering agent. Generally, any suitable acidic buffer can be used as the buffering agent if it is capable of adjusting the pH of the test solution to a pH which is near or within the color change range of the particular indicator. For example, if the indicator used is tetrabromphenol blue, which indicator is responsive in a pH range of about 3.0 to about 4.5, the buffer must be capable of buffering the test solution to a pH within or slightly below this range. Buffering agents found suitable in the present invention include the following acids, together with the salts thereof: citric acid, tartaric acid, maleic acid, oxalic acid, phosphoric acid and malic acid. The selection of a buffering agent, it should be recognized, is within the descretion of one skilled in the art. However, in the present device, the preferred buffering agent is a combination of sodium citrate and citric acid.

It will be recognized also by those skilled in the art that a wide range of materials and a wide range of proportions is possible with the device. However, by the use of routine experimentation, the necessary proportions of the ingredients of the invention can be readily determined by one skilled in the art.

In practice, the selected indicator and buffering agent are incorporated into or upon the carrier member to form a readily usable dip-and-read type device. This may be easily accomplished by preparing a solution of the indicator and the buffering agent and saturating the carrier member therewith. The carrier member is then dried for storage or use.

The prepared test device may then be used by dipping it into the solution to be tested and immediately withdrawing it therefrom to prevent leaching of the indicator and buffer. The carrier member will absorb enough of the test solution to provide enough sample of the solution to enable the indicator to change color if antifreeze is present in the solution. A visible color change of the device not only indicates the presence of antifreeze in the solution; the intensity or shade of the developed color is indicative of the concentration of antifreeze in the solution. This concentration may be easily converted to the freeze point of the solution.

To enable one to correlate the color change of the device to the freeze point of the solution, a color chart standardized for this purpose is used. The color chart indicates freeze point determinations for various concentrations of antifreeze solutions and provides a corresponding color therefor produced by the indicator and buffer combination of the specific device employed. Thus, by simply comparing to the corresponding color on the chart the color developed by the test device after a momentary immersion thereof into the antifreeze-containing solution, the operator is provided with a ready indication of the freeze point of the solution tested. The improved method, employing only the amount of solution absorbed by the carrier, thus enables any operator to perform the test without the need to return the test solution, for economy purposes, to the radiator or container from which it came.

The following examples will serve to illustrate test devices useful in practicing the method of this invention and are not intended to limit the inventive concept as herein disclosed.

EXAMPLE I

Test devices for determining the freeze point of antifreeze-containing solutions were prepared as follows:

20 mg. of tetrabromphenol blue was dissolved in 30 ml. of 95% ethanol. A second solution was prepared by dissolving 5.0 gm. of sodium citrate and 8.7 gm. of citric acid in 60 ml. of water. The two solutions were then combined and used to impregnate Eaton and Dickman No. 201 paper. The impregnated paper was dried at about 50°C. for about 10 minutes in a forced air oven. The dried paper was then cut into strips measuring ¼ inch wide by 6 inches long and placed in a dark, air-tight bottle.

A color or reference chart for the above prepared test devices was prepared by preparing six different aqueous solutions, each solution containing a different concentration of ethylene glycol. The solutions contained respectively 0, 25, 33, 40, 50 and 60% by weight of ethylene glycol. Momentary immersion of a separate test device into each solution developed a different color at each concentration. The colors developed were, in order of increasing concentration of ethylene glycol, yellow, greenish-yellow, lime, light green, turquoise green and blue turquoise respectively. The freeze point of each of the solutions was established with an Automotive Tester, a refractometer, marketed by American Optical Company of Buffalo, N.Y., and the approximate freezing points assigned to the respective solutions were +30°, +10°, 0°, −10°, −30°, and −60°F.

Thus the development of the following listed colors on the test devices indicated the following corresponding listed freeze points:

| Color | Concentration of Ethylene Glycol | Freeze Point (°F) |
| --- | --- | --- |
| yellow | 0% | +30 |
| greenish-yellow | 25% | +10 |
| lime | 33% | 0 |
| light green | 40% | −10 |
| turquoise green | 50% | −30 |
| turquoise blue | 60% | −60 |

EXAMPLE II

Three solutions containing 20, 30 and 45% by weight of methanol were prepared. Each solution was tested with a separate test device described in Example I. Each solution was also conventionally tested with a hydrometer to determine its freeze point. The colors developed by the test devices relative to the freeze point of the methanol solutions compared favorably with the colors and freeze points exhibited in Example I.

Thus, the development of the following listed colors on the test device upon immersion into the methanol solutions indicated the corresponding tested freeze points.

| Color | Concentration of Methanol | Freeze Point (°F) |
| --- | --- | --- |
| greenish-yellow | 20% | +10 |
| light green | 30% | −10 |
| turquoise green | 45% | −30 |

EXAMPLE III

To determine the compatability of the test devices of Example I with various commercial brands of antifreeze, freshly prepared dilutions of 21 different commercial brands were prepared. It was known that each brand contained a variety of dyes and perhaps other substances such as inhibitors or sealants which might interfere with the indicator of the devices.

Six different dilutions of each commercial brand were prepared. The dilutions respectively contained 25, 33, 40, 45, 50 and 60% by weight of the antifreeze in water. The freeze point of each dilution was determined by the refractometer described in Example I. These dilutions were then arranged in random fashion and were tested with the devices prepared in Example I. The results of these studies are shown in Table I which summarizes the results by grouping the dilutions into three categories by the refractometer-determined freeze points.

Table I

| F.P. Test Device Reading | +20° to −20° | | | −21° to −40° | | | −41° to −60° | | |
| --- | --- | --- | --- | --- | --- | --- | --- | --- | --- |
| | Over 10° Warmer | Within ±10° | Over 10° Colder | Over 10° Warmer | Within ±10° | Over 10° Colder | Over 15° Warmer | Within ±15° | Over 15° Colder |
| Brand | | | | | | | | | |
| 1 | 0 | 31 | 9 | 0 | 5 | 5 | 0 | 10 | 0 |
| 2 | 0 | 30 | 0 | 6 | 14 | 0 | 6 | 14 | 0 |
| 3 | 5 | 25 | 0 | 6 | 14 | 0 | 0 | 10 | 0 |
| 4 | 2 | 26 | 2 | 0 | 5 | 5 | 0 | 19 | 1 |
| 5 | 0 | 29 | 1 | 1 | 16 | 3 | 0 | 10 | 0 |
| 6 | 0 | 29 | 1 | 3 | 16 | 1 | 0 | 10 | 0 |
| 7 | 3 | 33 | 0 | 1 | 6 | 2 | 1 | 8 | 0 |
| 8 | 3 | 37 | 0 | 5 | 4 | 1 | 5 | 5 | 0 |
| 9 | 0 | 38 | 2 | 0 | 7 | 3 | 0 | 10 | 0 |
| 10 | 0 | 30 | 0 | 2 | 14 | 4 | 0 | 10 | 0 |
| 11 | 1 | 34 | 5 | 4 | 6 | 0 | 7 | 3 | 0 |
| 12 | 0 | 26 | 4 | 0 | 16 | 4 | 0 | 10 | 0 |

Table I-continued

| F.P. Test Device Reading | +20° to −20° ||| −21° to −40° ||| −41° to −60° |||
|---|---|---|---|---|---|---|---|---|---|
| | Over 10° Warmer | Within ±10° | Over 10° Colder | Over 10° Warmer | Within ±10° | Over 10° Colder | Over 15° Warmer | Within ±15° | Over 15° Colder |
| 13 | 0 | 34 | 2 | 0 | 9 | 0 | 1 | 17 | 0 |
| 14 | 1 | 39 | 0 | 5 | 5 | 0 | 3 | 7 | 0 |
| 15 | 4 | 26 | 0 | 6 | 13 | 1 | 0 | 10 | 0 |
| 16 | 1 | 29 | 0 | 2 | 18 | 0 | 2 | 8 | 0 |
| 17 | 0 | 28 | 2 | 0 | 14 | 6 | 0 | 19 | 1 |
| 18 | 1 | 38 | 1 | 0 | 10 | 0 | 0 | 10 | 0 |
| 19 | 0 | 30 | 0 | 7 | 12 | 1 | 0 | 10 | 0 |
| 20 | 1 | 28 | 1 | 0 | 15 | 5 | 1 | 9 | 0 |
| 21 | 0 | 22 | 5 | 0 | 16 | 2 | 0 | 9 | 0 |
| Totals | 22 | 642 | 35 | 48 | 235 | 43 | 26 | 218 | 2 |

F.P. - Freeze Point

Ninety-two percent of the readings with the test devices were within ±10°F. of the refractometer readings in the samples having freeze points between +20° and −20°F. Seventy-two percent of the test device readings were within ±10°F. in the dilutions having freeze points ranging from −21° to −40°F; and 89% of the reading with the test devices were within ±15°F. of the refractometer determined freezing point for those dilutions having freeze points ranging from a −41° to a −60°F.

In summary, a unique method has been disclosed for determining the freeze point of an antifreeze-containing solution, which method includes the steps of dipping into such a solution a carrier member having incorporated therewith a pH indicator and a buffering agent, and comparing the color developed on the member against a color chart standardized to show the freeze point corresponding to the developed color.

What is claimed is:

1. A method for determining the freeze point of an antifreeze-containing solution comprising the steps of:

immersing momentarily into the antifreeze-containing solution to be tested a bibulous material having incorporated therewith a pH indicator and a buffering agent;

removing the material from the solution; and then comparing any change in color of the bibulous material to a color chart standardized for freeze point determinations.

2. A method as defined in claim 1 wherein said indicator is selected from the group consisting of tetrabromphenol blue, bromphenol blue, tetrabromophenolphthalein ethyl ester and congo red.

3. A method as defined in claim 2 wherein said indicator is tetrabromphenol blue.

4. A method as defined in claim 1 wherein said buffering agent is selected from the group consisting of citric acid, tartaric acid, maleic acid, oxalic acid, phosphoric acid and malic acid, and the salts thereof.

5. A method as defined in claim 4 wherein said buffering agent is a combination of citric acid and a citric acid salt.

* * * * *